United States Patent [19]
Thompson et al.

[11] Patent Number: 6,030,715
[45] Date of Patent: Feb. 29, 2000

[54] AZLACTONE-RELATED DOPANTS IN THE EMISSIVE LAYER OF AN OLED

[75] Inventors: Mark Thompson, Anaheim; Yujian You, South Pasadena; Nicos A. Petasis, Hacienda Heights, all of Calif.; Paul E. Burrows, Princeton Junction; Stephen R. Forrest, Princeton, both of N.J.

[73] Assignees: The University of Southern California, Los Angeles, Calif.; The Trustees of Princeton University, Princeton, N.J.

[21] Appl. No.: 08/948,130

[22] Filed: Oct. 9, 1997

[51] Int. Cl.$^7$ .................................................. H05B 33/13
[52] U.S. Cl. ........................ 428/690; 428/691; 428/917; 313/504; 313/506
[58] Field of Search ..................... 428/690, 691, 428/917; 313/504, 506

[56] References Cited

U.S. PATENT DOCUMENTS 5,457,565  10/1995  Namiki et al. .

FOREIGN PATENT DOCUMENTS

96/19792  6/1996  WIPO .

OTHER PUBLICATIONS

Bulovic et al., "Transparent Light–emitting Devices", Nature 380, 29 (1996).
Whitlock et al., "Investigations of Materials and Device Structures for Organic Semiconductor Solar Cells", Optical Eng., vol. 32, No. 8, 1921–1934 (Aug. 1993).
C.W. Tang et al., "Organic electroluminescent diodes," Appl. Phys. Lett. 51 (12), Sep. 21, 1987.
S.R. Forrest et al., "Organic emitters promise a new generation of displays," Laser Focus World, Feb. 1995.
R. Heim et al., "Improved green fluorescence," Nature (1995/373, 663–664). No month.
Heim et al., "Wavelength mutations and posttranslational autoxidation of green fluorescent protein," Proc. Nat. Acad. Sci. (1994) 91, 12501–12504.
Rao et al., "Geometric Isomers of 2–Aryl(Aralkyl)–4–arylidene(alkyidene)–5(4H)–oxazolones," Synthesis (1975) 749–764. No month.

*Primary Examiner*—Charles Nold
*Attorney, Agent, or Firm*—Kenyon & Kenyon

[57] ABSTRACT

Organic light emitting devices are disclosed which are comprised of a heterostructure for producing electoluminescence wherein the heterostructure is comprised of an emissive layer containing a dopant compound selected from the class of azlactone-related compounds having the chemical structure as represented by formula I:

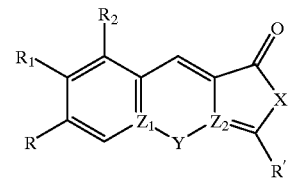

where R is hydrogen or a donor or acceptor group relative to hydrogen;
R'=alkyl or substituted or unsubstituted aryl;
$R_1$ and $R_2$ are hydrogen or are joined to form a fused aryl ring;
X is O; $NR_5$, where $R_5$ is hydrogen or substituted or unsubstituted alkyl; alkyl or substituted or unsubstituted aryl;
$Z_1$ and $Z_2$ are, independently of one another, a carbon or nitrogen atom; and
Y is M, a metal atom, whenever $Z_1$ and $Z_2$ are both nitrogen atoms;
Y is O; $NR_6$, where $R_6$ is hydrogen or substituted or unsubstituted alkyl; or S; whenever either $Z_1$ or $Z_2$ is a carbon atom; or
Y is absent.

19 Claims, 1 Drawing Sheet

AZLACTONE-RELATED DOPANTS IN THE EMISSIVE LAYER OF AN OLED

FIELD OF INVENTION

The present invention is directed to organic light emitting devices (OLEDs) comprised of emissive layers that contain azlactone-related dopants.

BACKGROUND OF THE INVENTION

Organic light emitting devices (OLEDs) are comprised of several organic layers in which one of the layers is comprised of an organic material that can be made to electroluminesce by applying a voltage across the device, C. W. Tang et al., *Appl. Phys. Lett* 51, 913 (1987). Certain OLEDs have been shown to have sufficient brightness, range of color and operating lifetimes for use as a practical alternative technology to LCD-based full color flat-panel displays (S. R. Forrest, P. E. Burrows and M. E. Thompson, Laser Focus World, Feb. 1995). Since many of the thin organic films used in such devices are transparent in the visible spectral region, they allow for the realization of a completely new type of display pixel in which red (R), green (G), and blue (B) emitting OLEDs are placed in a vertically stacked geometry to provide a simple fabrication process, a small R-G-B pixel size, and a large fill factor.

A transparent OLED (TOLED), which represents a significant step toward realizing high resolution, independently addressable stacked R-G-B pixels, was reported in International Patent Application No. PCT/US95/15790. This TOLED had greater than 71% transparency when turned off and emitted light from both top and bottom device surfaces with high efficiency (approaching 1% quantum efficiency) when the device was turned on. The TOLED used transparent indium tin oxide (ITO) as the hole-injecting electrode and a Mg—Ag—ITO electrode layer for electron-injection. A device was disclosed in which the ITO side of the Mg—Ag—ITO electrode layer was used as a hole-injecting contact for a second, different color-emitting OLED stacked on top of the TOLED. Each layer in the stacked OLED (SOLED) was independently addressable and emitted its own characteristic color. This colored emission could be transmitted through the adjacently stacked transparent, independently addressable, organic layer, the transparent contacts and the glass substrate, thus allowing the device to emit any color that could be produced by varying the relative output of the red and blue color-emitting layers.

The PCT/US95/15790 application disclosed an integrated SOLED for which both intensity and color could be independently varied and controlled with external power supplies in a color tunable display device. The PCT/US95/15790 application, thus, illustrates a principle for achieving integrated, full color pixels that provide high image resolution, which is made possible by the compact pixel size. Furthermore, relatively low cost fabrication techniques, as compared with prior art methods, may be utilized for making such devices.

Such devices whose structure is based upon the use of layers of organic optoelectronic materials generally rely on a common mechanism leading to optical emission. Typically, this mechanism is based upon the radiative recombination of a trapped charge. Specifically, OLEDs are comprised of at least two thin organic layers separating the anode and cathode of the device. The material of one of these layers is specifically chosen based on the material's ability to transport holes, a "hole transporting layer" (HTL), and the material of the other layer is specifically selected according to its ability to transport electrons, an "electron transporting layer" (ETL). With such a construction, the device can be viewed as a diode with a forward bias when the potential applied to the anode is higher than the potential applied to the cathode. Under these bias conditions, the anode injects holes (positive charge carriers) into the hole transporting layer, while the cathode injects electrons into the electron transporting layer. The portion of the luminescent medium adjacent to the anode thus forms a hole injecting and transporting zone while the portion of the luminescent medium adjacent to the cathode forms an electron injecting and transporting zone. The injected holes and electrons each migrate toward the oppositely charged electrode. When an electron and hole localize on the same molecule, a Frenkel exciton is formed. Recombination of this short-lived state may be visualized as an electron dropping from its conduction potential to a valence band, with relaxation occurring, under certain conditions, preferentially via a photoemissive mechanism. Under this view of the mechanism of operation of typical thin-layer organic devices, the electroluminescent layer comprises a luminescence zone receiving mobile charge carriers (electrons and holes) from each electrode.

The materials that function as the electron transporting layer of the OLED are frequently the same materials that are incorporated into the OLED to produce the electroluminescent emission. Such devices in which the electron transporting layer functions as the emissive layer are referred to as having a single heterostructure. Alternatively, the electroluminescent material may be present in a separate emissive layer between the hole transporting layer and the electron transporting layer in what is referred to as a double heterostructure.

In addition to emissive materials that are present as the predominant component in the electron transporting layer, and that function both as the electron transporting material as well as the emissive material, the emissive material may itself be present in relatively low concentrations as a dopant in the electron transporting layer. Whenever a dopant is present, the predominant material in the electron transporting layer may be referred to as a host material. Materials that are present as host and dopant are selected so as to have a high level of energy transfer from the host to the dopant material. In addition, these materials need to be capable of producing acceptable electrical properties for the OLED. Furthermore, such host and dopant materials are preferably capable of being incorporated into the OLED using starting materials that can be readily incorporated into the OLED by using convenient fabrication techniques, in particular, by using vacuum-deposition techniques.

It is desirable for OLEDs to be fabricated using materials that provide electroluminescent emission in a relatively narrow band centered near selected spectral regions, which correspond to one of the three primary colors, red, green and blue so that they may be used as a colored layer in an OLED or SOLED. It would be desirable, in particular, to be able to select these compounds from a class of compounds in which the emission may be varied by selectively varying the substituents or by modifying the structure of a base compound that produces emission from a charge transfer transition. It is furthermore desirable that such compounds also be capable of being readily deposited as a thin layer using vacuum deposition techniques so that it may be readily incorporated into an OLED that is prepared entirely from vacuum-deposited organic materials.

A recent article disclosed a jelly fish (*Aequorea Victoria*) which gives very narrow green fluorescence, R. Heim, A. B.

Cubitt, and R. Y. Tsien, *Nature* (1995) 373, 663–664. The reported spectrum was centered at roughly 510 nm with a half width of 40 nm and the active chromophore responsible for this emission was shown to be:

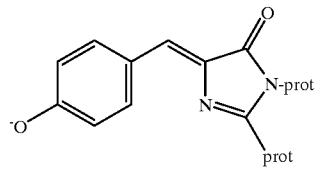

This p-hydroxybenzylidene-imidazolidinone chromophore is reported to be generated by cyclization and oxidation of the protein's own Ser-Tyr-Gly sequence and is bound to the protein in two places, labeled as "prot". Mutants of the protein have been reported which produce emission which is significantly blue shifted. It was proposed that the blue shift is due to changes in the protein matrix to which the dye is bound rather than to changes in the dye itself, R. Heim, D. C. Prasher, and R. Y. Tsien, *Proc. Nat. Acad. Sci.* (1994) 91, 12501–12504. The fluorescence in these dyes is from a donor/acceptor network, involving a phenoxide ion donor and a carbonyl acceptor. The Heim publications describe use of the chromophores for labeling proteins with fluorescent tags to detect their localization or conformational changes both in vitro and in intact cells. However, these publications disclose nothing about preparation or use of the isolated chromophore molecule itself.

The present invention is directed to a class of azlactone-related compounds that may be used as a dopant in the emissive layer of an OLED in which the emission of the dopant may be varied by selectively varying the substituents or by modifying the structure of the base compound that produces the emission. Such compounds are capable of being readily deposited as a thin layer using vacuum deposition techniques so that it may be readily incorporated into an OLED that is prepared entirely from vacuum-deposited organic materials. A review article summarizing azlactones discloses nothing about the fluorescent properties and nothing about a utility for these compounds, Y. S. Rao and R. Filler, *Synthesis* (1975) 749–764.

ADVANTAGES AND SUMMARY OF THE INVENTION

The present invention is directed to a class of azlactone-related compounds that may be used as a dopant in the emissive layer of an OLED.

More specifically, the present invention is directed to dopant compounds selected from a class of azlactone-related compounds that produce electroluminescence in bands centered in the wavelength region of one of the primary colors.

In addition, the present invention is directed to an organic light emitting device, and to a method of fabricating an organic light emitting device, comprising a heterostructure for producing electoluminescence wherein the heterostructure is comprised of an emissive layer containing an azlactone-related compound.

Further objectives and advantages of the present invention will be apparent to those skilled in the art from the detailed description of the disclosed invention.

DETAILED DESCRIPTION OF THE PREFERRED EMBODIMENTS

Figure 1:
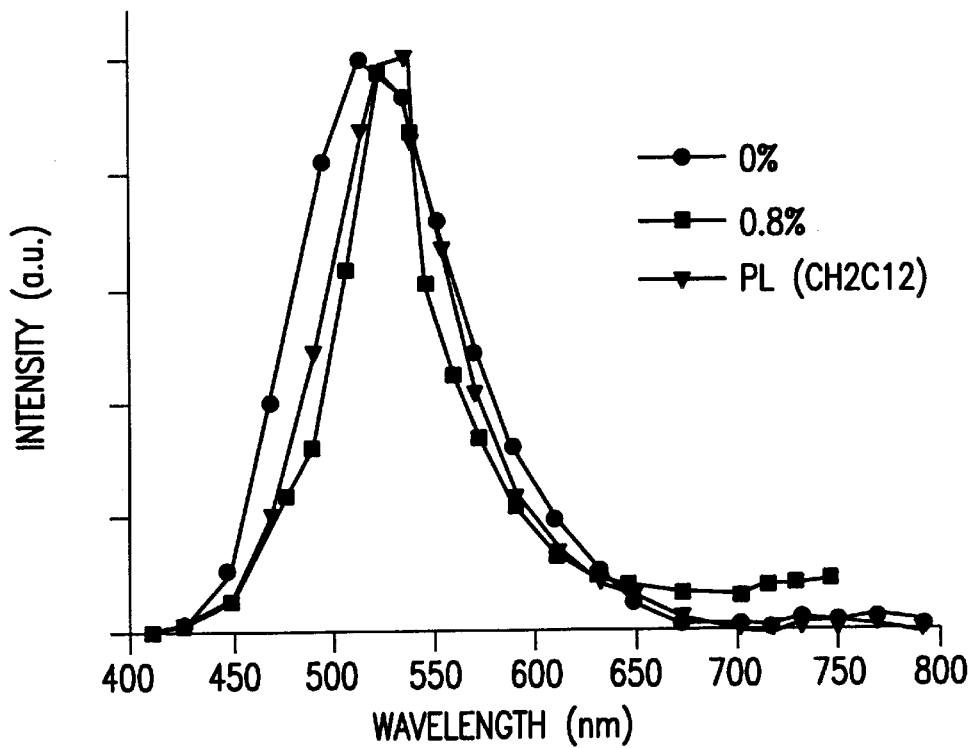
FIG. 1 shows the electroluminescent spectra of a device doped with 0.8% of Compound 3 as dopant and an undoped $Alq_3$ device ("0%"), as compared with the photoluminescent spectrum of the dopant when present in $CH_2Cl_2$.

The present invention will now be described in detail for specific preferred embodiments of the invention, it being understood that these embodiments are intended only as illustrative examples and the invention is not to be limited thereto.

The present invention is directed toward OLEDs comprised of an emissive layer comprised of a dopant compound selected from the class of azlactone-related compounds having the chemical structure of formula I:

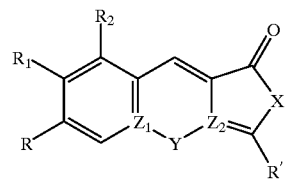

(I)

where R is hydrogen or a group which is a donor or acceptor group relative to hydrogen;

R'=alkyl or substituted or unsubstituted aryl;

$R_1$ and $R_2$ are hydrogen or are joined to form a fused aryl ring;

X is O; $NR_5$, where $R_5$ is hydrogen or substituted or unsubstituted alkyl; alkyl or substituted or unsubstituted aryl;

$Z_1$ and $Z_2$ are, independently of one another, a carbon or nitrogen atom; and Y is M, a metal atom, whenever $Z_1$ and $Z_2$ are both nitrogen atoms;

Y is O; $NR_6$, where $R_6$ is hydrogen or substituted or unsubstituted alkyl; or S; whenever either $Z_1$ or $Z_2$ is a carbon atom; or Y is absent.

Representative donor groups include the n-electron donor groups such as —OR, —Br, —$NR_3R_4$, where $R_3$ and $R_4$ are, independently of one another, hydrogen or substituted or unsubstituted alkyl. Representative acceptor groups include the π-electron acceptor groups such as —CN, —$NO_2$ or a carbonyl-containing group.

As a more specific representative embodiment, the present invention is directed to an OLED comprising an emissive layer comprised of a dopant azlactone-based compound having the chemical structure of formula II:

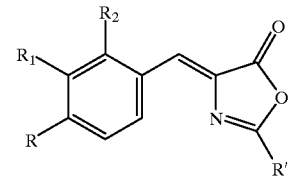

(II)

where R, R', $R_1$ and $R_2$ have the same meaning as above.

As a further still more specific representative embodiment, the present invention is directed to an OLED comprising an emissive layer comprised of a dopant azlactone-based compound having the chemical structure of formula III:

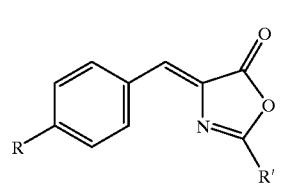

(III)

where R and R' have the same meaning as above.

Still more specifically, the dopant azlactone-based compound may have the chemical structure of formula III wherein R=H and R'=$C_6H_5$ (Compound 1); R=OOCCH$_3$ and R'=$C_6H_5$ (Compound 2); R=N(CH$_3$)$_2$ and R'=$C_6H_5$ (Compound 3); and R=C(CH$_3$)$_3$ and R'=$C_6H_5$ (Compound 4).

As still another specific embodiment of the present invention, the dopant azlactone-based compound may have the chemical structure of formula IV:

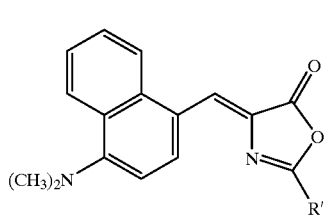

(IV)

where R'=$C_6H_5$ (Compound 5).

As yet other specific embodiment of the present invention, the dopant azlactone-based compound may have a chemical structure of formula V (Compound 6):

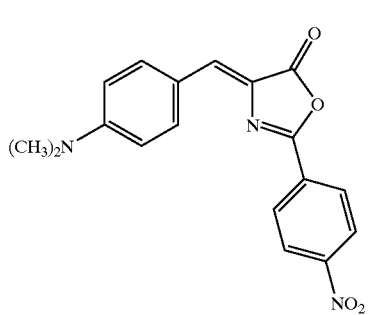

(V)

or a chemical structure of formula VI (Compound 7):

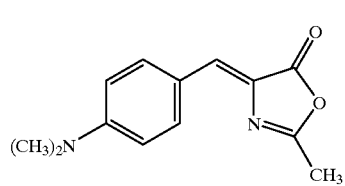

(VI)

These azlactone-based compounds may be prepared from para-substituted benzaldehyde and hippuric acid derivatives. By varying the para-substituted donor group, the emission can be tuned from the green into the blue part of the spectrum, as illustrated by the results in Table 1 below.

TABLE 1

Fluorescence data showing the absorption maxima and the photoluminescence (PL) maxima for compounds 1–7.

| | Abs. Max. (nm) | PL Max. (nm) |
|---|---|---|
| Compound 1 | 364 (CH$_2$Cl$_2$) | 416 (CH$_2$Cl$_2$) |
| | 367 (DMSO) | |
| Compound 2 | 368 (CH$_2$Cl$_2$) | 422 (CH$_2$Cl$_2$) |
| Compound 3 | 471 (CH$_2$Cl$_2$) | 522 (CH$_2$Cl$_2$) |
| | 481 (DMSO) | 552 (DMSO) |
| | 464 (hexane) | 464 (hexane) |
| | 467 (toluene) | 500 (toluene) |
| Compound 4 | 373 (CH$_2$Cl$_2$) | 428 (CH$_2$Cl$_2$) |
| | 374 (DMSO) | |
| Compound 5 | 368 (CH$_2$Cl$_2$) | 518 (CH$_2$Cl$_2$, excit. = 360 nm) |
| | 471 (shoulder, CH$_2$Cl$_2$) | 582 (CH$_2$Cl$_2$, excit. = 470 nm) |
| Compound 6 | 513 (CH$_2$Cl$_2$) | 734 (CH$_2$Cl$_2$, excit. = 320 nm) |
| | | 752 (CH$_2$Cl$_2$, excit. = 520 nm) |
| | 518 (DSMO) | 406 (DSMO) |
| | 498 (hexane) | 524 (hexane) |
| | 499 (toluene) | 602 (toluene) |
| Compound 7 | 438 (DMSO) | very weak emission |

The color of the fluorescence from the materials shown in Table 1 is strongly solvent dependent as is expected for emission from a charge transfer transition.

Still other specific examples of dopant azlactone-based compounds include the chemical structure of formula III wherein R=OH and R'=$C_6H_5$ and the compound having the chemical structure of formula III wherein R=C(CH$_3$)$_3$ and R'=CH$_3$.

Compound 6 is an example of a compound having a charge transfer network different from that of the derivatives of Compound 1. Emission in this case comes from the amine donor and nitro group acceptor. This dye can be pumped either in the blue or in the green to get red emission, as shown for Compound 6 in CH$_2$Cl$_2$. Compound 6 illustrates that these dyes can have different excitation wavelengths leading to red emission. Though the PL efficiency for this dye is very poor, derivatives with other acceptors are expected to be capable of increasing this efficiency.

The line widths observed in the doped OLED for a representative compound of formulas II or III, Compound 3, are narrower than those seen for Alq$_3$ alone, but are broader than those observed in solution. The reason for this is believed to be that in solution the molecule is free to adopt the planar structure suggested by the scheme shown in Formula II, while in the solid state there tends to be distribution of dihedral angles about the bond connecting the phenyl ring bearing the dimethylamino group to the carbonyl moiety. This dispersion gives rise to a range of energies for both absorption and fluorescence and increases the linewidth observed. This dispersion also decreases the overall fluorescence quantum yield.

In order to prevent this solid state broadening, materials may be used which have a locked chemical configuration comprised of a rigid or locked molecule as shown in Formula I. In these compounds, the ring groups are held coplanar by the Y group. Thus, while the present invention is demonstrated with respect to the representative embodiments of the azlactone-based compounds of formulas II or III, the azlactone-related compounds of formula I also fall fully within the spirit and scope of the present invention. The azlactone-related compounds embraced by formula I include, but are not limited to, the azlactone-based compounds of formulas II and III.

The present invention is further directed to the azlactone-related compounds of formula I:

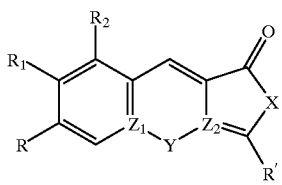

(I)

where R is hydrogen or a group which is a donor or acceptor group relative to hydrogen;

R'=alkyl or substituted or unsubstituted aryl;

$R_1$ and $R_2$ are hydrogen or are joined to form a fused aryl ring;

X is O; $NR_5$, where $R_5$ is hydrogen or substituted or unsubstituted alkyl; alkyl or substituted or unsubstituted aryl;

$Z_1$ and $Z_2$ are, independently of one another, a carbon or nitrogen atom; and Y is M, a metal atom, whenever $Z_1$ and $Z_2$ are both nitrogen atoms;

Y is O; $NR_6$, $R_6$ is hydrogen or substituted or unsubstituted alkyl; or S; whenever either $Z_1$ or $Z_2$ is a carbon atom; or Y is absent; with the proviso that, whenever Y is absent, $Z_1$ is a carbon atom and $Z_2$ is a nitrogen atom, then R is a group which is a donor or acceptor group relative to hydrogen.

As a more specific representative embodiment of the compounds of the present invention, the present invention is directed to an azlactone-based compound having the chemical structure of formula II:

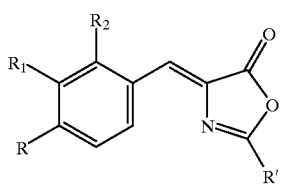

(II)

where R is a group which is a donor or acceptor group relative to hydrogen;

R'=alkyl or substituted or unsubstituted aryl; and $R_1$ and $R_2$ are hydrogen or are joined to form a fused aryl ring.

As a still more specific representative embodiment of the compounds of the present invention, the present invention is directed to an azlactone-based compound having the chemical structure of formula III:

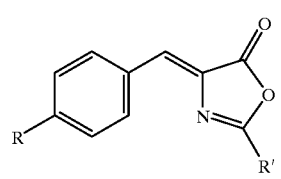

(III)

where R is a group which is a donor or acceptor group relative to hydrogen; and

R'=alkyl or substituted or unsubstituted aryl.

A dopant capable of shifting the emission wavelength of an emissive layer comprised only of a host compound is added to the host compound in an amount effective to shift the wavelength of emission so that the LED device preferably emits light that is perceived by the human eye to be close to one of the primary colors. Although it is recognized that characterization of color perception is a subjective exercise, a quantitative chromaticity scale has been developed by the Commission Internationale de l'Eclairage (International Commission of Illumination), otherwise known as the CIE standard. According to this standard, a saturated color may be represented by a single point, with specific quantitative coordinates according to the defined axes of the chromaticity scale. It will be appreciated by one of skill in the art that such a single point on the CIE scale would represent a standard or a goal that, in practical terms, is difficult, but fortunately, unnecessary, to attain.

In the preferred embodiments of the present invention in which the OLED predominantly produces a primary color, the dopant is incorporated into a host compound so that the OLED emits light that is perceived by the human eye to be close to a saturated primary color. Through the practice of the present invention, it is intended that OLEDs be constructed which can be characterized by an emission that is close to an absolute (or saturated) chromaticity value, as that would be defined by the CIE scale. Furthermore, LED's utilizing the materials of the present invention are also intended to be capable of a display brightness that can be in excess of 100 cd/m² although somewhat lower values, perhaps as low as 10 cd/m², may be acceptable in certain cases.

The host compounds as defined herein are compounds which can be doped with dopants to emit light with the desired spectral characteristics. Such compounds include, but are not limited to, both emitting compounds and host compounds as described in U.S. patent application Ser. No. 08/693,359, filed 6 August 1996, incorporated herein by reference. The term "host" is used to refer to the compound in the emissive layer that functions as the component which receives the hole/electron recombination energy and then by an emission/absorption energy transfer process, transfers that excitation energy to the dopant compound, which is typically present in much lower concentrations. The dopant may then relax to an excited state having a slightly lower energy level, which preferentially radiates all of its energy as luminescent emission in a desired spectral region. A dopant that radiates 100% of the dopant's excited state excitation energy is said to have a quantum efficiency of 100%. For host/dopant concentrations which are to be used in a color tunable SOLED, preferably most, if not all, of the host's excitation energy is transferred to the dopant which in turn radiates, perhaps from a lower energy level, but with a high quantum efficiency, to produce visible radiation having a desired chromaticity. The present invention is directed toward classes of azlactone-related compounds that are intended to serve as dopants which satisfy these demanding energy transfer requirements.

As the term host compound is used herein, it will be appreciated that such compounds can be found in either an electron transporting/emissive layer of a single heterostructure OLED device or in the separate emissive layer of a double heterostructure device. As will be recognized by one of skill in the art, use of the dopant species such as disclosed herein makes it possible to extend not only the range of colors emitted by the OLED, but also to extend the range of possible candidate species for host and/or dopant compounds. Accordingly, for effective host/dopant systems, although the host compound can have a strong emission in a region of the spectrum where the dopant species strongly absorbs light, the host species preferably does not have an emission band in a region where the dopant also emits strongly. In structures where the host compound also functions as a charge carrier, then additional criteria such as redox potential for the species also becomes a consideration. In general, however, the spectral characteristics of the host and dopant species are the most important criteria.

The amount of dopant that is present is that amount which is sufficient to shift the emission wavelength of the host material as close as possible to a saturated primary color, as that would be defined according to the CIE scale. Typically, the effective amount is from about 0.01 to 10.0 mol %, based on the emitting layer. The preferred amount is from about 0.1 to 1.0 mol %. The primary criterion for determining an appropriate doping level is the level which is effective for achieving an emission with the appropriate spectral characteristics. By way of example, and without limitation, if the amount of dopant species is at too low a level, then emission from the device will also comprise a component of light from the host compound itself, which will be at shorter wavelengths than the desired emission form the dopant species. In contrast, if the level of dopant is too high, emission efficiencies could be adversely affected by self-quenching, a net non-emissive mechanism. Alternatively, too high levels of the dopant species could also adversely affect the hole or electron transporting properties of the host material.

The OLEDs of the present invention are comprised of a heterostructure for producing electroluminescence which may be fabricated as a single heterostructure or as a double heterostructure. The materials, methods and apparatus for preparing the organic thin films of a single or double heterostructure are disclosed, for example, in U.S. Pat. No. 5,554,220, which is incorporated herein in its entirety by reference. In particular, the present invention is directed toward OLEDs which include a heterostructure for producing electroluminescence wherein the heterostructure includes an emissive layer containing a dopant compound selected from the class of azlactone-related compounds having the chemical structure of formula I.

As used herein, the term "heterostructure for producing electroluminescence" refers to a heterostructure that includes, for a single heterostructure, a substrate, a hole injecting anode layer in contact with the substrate, a hole transporting layer in contact with the anode layer, an electron transporting layer in contact with the hole transporting layer, and an electrode injecting cathode layer in contact with the hole electron transporting layer. If the cathode layer is a metal cathode layer of Mg:Ag, then a metal protective layer, for example, made of a layer of Ag for protecting the Mg:Ag cathode layer from atmospheric oxidation, may also be present. If a double heterostructure is used to produce electroluminescence, a separate emissive layer is included between the hole transporting layer and the electron transporting layer.

Whenever the OLED is comprised of a double heterostructure having an additional layer of emissive material between the hole transporting and electron transporting layers, this additional layer is referred to as a "separate emissive layer" so as to distinguish it from the electron transporting layer of a single heterostructure that functions both as the electron transporting layer as well as the emissive layer that produces the electroluminescence. The term "emissive layer" as used herein, thus, may refer either to the emissive, electron transporting layer of a single heterostructure or the separate emissive layer of a double heterostructure.

Alternatively, the heterostructure for producing electroluminescence may have an inverted (IOLED) structure in which the sequence of layers deposited on the substrate is inverted, that is, an electron injecting cathode layer is in direct contact with the substrate, an electron transporting layer is in contact with the cathode layer, a hole transporting layer is in contact with the electron transporting layer, and a hole injecting anode layer is in contact with the hole transporting layer.

If the heterostructure for producing electroluminescence is included as part of a stacked OLED (SOLED), one or both of the electrodes of an individual heterostructure may be in contact with an electrode of an adjacent heterostructure. Alternatively, dependent on the circuitry used to drive the SOLED, an insulating layer may be provided between adjacent electrodes of two of the OLEDs in the stack.

The single or double heterostructures as referred to herein are intended solely as examples for showing how an OLED embodying the present invention may be fabricated without in any way intending the invention to be limited to the particular materials or sequence for making the layers shown. For example, a single heterostructure typically includes a substrate which may be opaque or transparent, rigid or flexible, and/or plastic, metal or glass; a first electrode, which is typically a high work function, hole-injecting anode layer, for example, an indium tin oxide (ITO) anode layer; a hole transporting layer; an electron transporting layer; and a second electrode layer, for example, a low work function, electron-injecting, metal cathode layer of a magnesium-silver alloy, (Mg:Ag) or of a lithium-aluminum alloy, (Li:Al).

Materials that may be used as the substrate in a representative embodiment of the present invention include, in particular, glass, transparent polymer such as polyester, sapphire or quartz, or substantially any other material that may be used as the substrate of an OLED.

Materials that may be used as the hole-injecting anode layer in a representative embodiment of the present invention include, in particular, ITO, Zn—In—$SnO_2$ or $SbO_2$, or substantially any other material that may be used as the hole-injecting anode layer of an OLED.

Materials that may be used in the hole transporting layer in a representative embodiment of the present invention include, in particular, N,N'-diphenyl-N,N'-bis(3-methylpheny)1-1'biphenyl-4,4'diamine (TPD), 4,4'-bis[N-(1-naphthyl)-N-phenyl-amino]biphenyl ($\alpha$-NPD) or 4,4'-bis [N-(2-naphthyl)-N-phenyl-amino]biphenyl ($\beta$-NPD). Other materials that may be used as the electron transporting layer include, in particular, tris-(8-hydroxyquinoline)-aluminum ($Alq_3$) and carbazole. Other materials that may be used as the separate emissive layer, if present, include, in particular, dye-doped $Alq_3$, or substantially any other material that may be used as the separate emissive layer of an OLED.

Materials that may be used as the electron-injecting, metal cathode layer in a representative embodiment of the present invention include, in particular, Mg—Ag, Li—Ag or Ca, or substantially any other material that may be used as the cathode layer of an OLED.

The insulating layer, if present, may be comprised of an insulating material such as $SiO_2$, $SiN_x$ or $AlO_2$, or substantially any other material that may be used as the insulating material of an OLED, which may be deposited by a variety of processes such as plasma enhanced chemical vapor deposition (PECVD), electron beam, etc.

The OLEDs of the present invention have the advantage that they can be fabricated entirely from vacuum-deposited molecular organic materials as distinct, for example, from OLEDs in which some of the layers are comprised of polymeric materials, which cannot be readily deposited using vacuum deposition techniques. A vacuum-deposited material is one which can be deposited in a vacuum typically having a background pressure less than one atmosphere, preferably about $10^{-5}$ to about $10^{-11}$ torr for vacuum deposition, or about 50 torr to about $10^{-5}$ torr for vapor deposition.

Although not limited to the thickness ranges recited herein, the substrate may be as thin as 10 μ, if present as a flexible plastic or metal foil substrate, such as aluminum foil, or substantially thicker if present as a rigid, transparent or opaque, substrate or if the substrate is comprised of a silicon-based display driver; the ITO anode layer may be from about 500 D (1 D=$10^{-8}$ cm) to greater than about 4000 D thick; the hole transporting layer from about 50 D to greater than about 1000 D thick; the separate emissive layer of a double heterostructure, if present, from about 50 D to about 200 D thick; the electron transporting layer from about 50 D to about 1000 D thick; and the metal cathode layer from about 50 D to greater than about 100 D thick, or substantially thicker if the cathode layer includes a protective silver layer and is opaque.

Thus, while there may be substantial variation in the type, number, thickness and order of the layers that are present, dependent on whether the device includes a single heterostructure or a double heterostructure, whether the device is a SOLED or a single OLED, whether the device is a TOLED or an IOLED, whether the OLED is intended to produce emission in a preferred spectral region, or whether still other design variations are used, the present invention is directed to those devices in which the OLED is comprised of a heterostructure for producing electoluminescence wherein the heterostructure is comprised of an emissive layer containing a compound selected from the class of azlactone-related compounds having the chemical structure as represented by Formula I.

The subject invention as disclosed herein may be used in conjunction with co-pending applications: "High Reliability, High Efficiency, Integratable Organic Light Emitting Devices and Methods of Producing Same", Ser. No. 08/774,119 (filed Dec. 23, 1996); "Novel Materials for Multicolor Light Emitting Diodes", Ser. No. 08/850,264 (filed May 2, 1997); "Electron Transporting and Light Emitting Layers Based on Organic Free Radicals", Ser. No. 08/774,120 (filed Dec. 23, 1996); "Multicolor Display Devices", Ser. No. 08/772,333 (filed Dec. 23, 1996); "Red-Emitting Organic Light Emitting Devices (OLED's)", Ser. No. 08/774,087 (filed Dec. 23, 1996); "Driving Circuit For Stacked Organic Light Emitting Devices", Ser. No. 08/792,050 (filed Feb. 3, 1997); "High Efficiency Organic Light Emitting Device Structures", Ser. No. 08/772,332 (filed Dec. 23, 1996); "Vacuum Deposited, Non-Polymeric Flexible Organic Light Emitting Devices", Ser. No. 08/789,319 (filed Jan. 23, 1997); "Displays Having Mesa Pixel Configuration", Ser. No. 08/794,595 (filed Feb. 3, 1997); "Stacked Organic Light Emitting Devices", Ser. No. 08/792,046 (filed Feb. 3, 1997); "High Contrast Transparent Organic Light Emitting Device Display", Ser. No. 08/821,380 (filed Mar. 20, 1997); "Organic Light Emitting Devices Containing A Metal Complex of 5-Hydroxy-Quinoxaline as A Host Material", Ser. No. 08/838,099 (filed Apr. 15, 1997); "Light Emitting Devices Having High Brightness", Ser. No. 08/844,353 (filed Apr. 18, 1997); "Organic Semiconductor Laser", Ser. No. 08/859,468 (filed May 19, 1997); "Saturated Full Color Stacked Organic Light Emitting Devices", Serial No. 08/858,994 (filed on May 20, 1997); "An Organic Light Emitting Device Containing a Hole Injection Enhancement Layer", Ser. No. 08/865,491 (filed May 29, 1997); "Plasma Treatment of Conductive Layers", PCT/US97/10252, (filed Jun. 12, 1997); "Patterning of Thin Films for the Fabrication of Organic Multi-color Displays", PCT/US97/10289, (filed Jun. 12, 1997); "OLEDs Containing Thermally Stable Asymmetric Charge Carrier Materials", Ser. No. 08/929,029, filed Sep. 8, 1997; "Light Emitting Device with Stack of OLEDS and Phosphor Downconverter", Ser. No. 08/925,403, (filed Sep. 9, 1997); and "An Improved Method for Depositing Indium Tin Oxide Layers in Organic Light Emitting Devices", Ser. No. 08/928,800 (filed Sep. 12, 1997); each co-pending application being incorporated herein by reference in its entirety. The subject invention may also be used in conjunction with the subject matter of each of co-pending U.S. patent application Ser. Nos. 08/354,674, 08/613,207, 08/632,322 and 08/693,359 and provisional patent application Ser. Nos. 60/010,013, 60/024,001, 60/025,501, 60/046,061 and 60/053,176, each of which is also incorporated herein by reference in its entirety.

The materials that may be used as the substrate, the hole-injecting anode layer, the hole transporting layer, the electron transporting layer, the electron-injecting, metal cathode layer, the separate emissive layer if present, or the insulating layer, if present, include the materials as disclosed in these co-pending applications.

The OLED of the present invention may be used in substantially any type of device which is comprised of an OLED, for example, in OLEDs that are incorporated into a larger display, a vehicle, a computer, a television, a printer, a large area wall, theater or stadium screen, a billboard or a sign.

This invention will now be described in detail with respect to showing how certain specific representative embodiments thereof can be made, the materials, apparatus and process steps being understood as examples that are intended to be illustrative only. In particular, the invention is not intended to be limited to the methods, materials, conditions, process parameters, apparatus and the like specifically recited herein.

AN EXAMPLE OF THE INVENTION

The procedures that were used for fabrication of Organic Light-Emitting Devices (OLEDs) were as follows:

The hole transporting material TPD and the electron transporting material Alq$_3$ were synthesized according to known procedures, and were sublimed before use.

Compound 1: Hippuric acid (40.0 g, 0.22 mol), benzaldehyde (25.0 g, 0.24 mol), sodium acetate (16.0 g, 0.24 mol) and anhydrous acetic acid (120 ml, 1.2 mol) were mixed and well stirred for 3 days. The resulting yellow mixture was added to cold deionized water (1 L) and the yellow solid was collected by filtration. Yellow needles (48 g) were collected after crystallization from acetone (2 L). Yield: 88%. M.p.: 162–163EC. Anal. Cald.: C, 77.1; H, 4.45, N, 5.62. Found: 76.2, H, 4.47; N, 5.55. M.S.: 249 (P), 105 (PhCO), 77 (Ph). NMR (25EC, CDCl3): 8.15–8.30 (m), 7.47–7.65 (m).

Compound 2: Hippuric acid (5.0 g, 27.9 mmol), p-hydroxybenzaldehyde (3.70 g,30.3 mmol), sodium acetate (2.0 g, 30 mmol) and anhydrous acetic acid (20 ml, 212 mmol) were mixed and well stirred for a day. The resulting yellow mixture was added to cold deionized water (0.2 L) and the yellow solid was collected by filtration. Yellow crystals were collected after crystallization from acetone. M.S.: 307 (P), 265 (P—CH3COO+H), 105 (PhCO), 77 (Ph). NMR (25EC, CDCl3): 8.25 (d, 8.8 Hz), 8.18 (d, 8.0 Hz), 7.50–7.66 (m), 7.20–7.26 (m), 2.34 (s, Me).

Compound 3: Hippuric acid (5.00 g, 27.9 mmol), p-dimethylaminobenzaldehyde (4.38 g, 29.4 mmol), sodium acetate (2.0 g, 30 mmol) and anhydrous acetic acid (20 ml, 212 mmol) were mixed and well stirred for a day. The resulting deep red mixture was added to cold deionized water (200 mL) and the red solid was collected by filtration. Red crystals (1.0 g) were collected after crystallization from acetone and sublimation (200EC). Yield: 12%. M.p.: 211–213EC. Anal. Cald.: C, 74.0; H, 5.52, N, 9.58. Found: 73.9, H, 5.51; N, 9.54. M.S.: 292 (P), 159 (P—PhCOCO), 105 (PhCO), 77(Ph). NMR (25EC, CDCl3): 8.15 (dd, 8.3 Hz, 1.8 Hz), 7.46–7.56 (m), 7.22 (s), 6.82 (d, 8.75 Hz), 3.12 (s, Me).

Compound 4: Hippuric acid (8.57 g, 47.8 mmol), p-tert-butylbenzaldehyde (8.0 mL, 47.8 mmol), sodium acetate (3.2 g,48.5 mmol) and anhydrous acetic acid (35 ml, 317 mmol) were mixed and well stirred for two days. The resulting yellow mixture was added to cold deionized water (150 ml) and the yellow solid was collected by filtration and purified by crystallization from acetone and sublimation (160EC). Yield: 88%. M.p.: 142EC. Anal. Cald.: C, 78.7; H, 6.27, N, 4.58. Found: 78.7, H, 6.25; N, 4.58. M.S.: 305 (P), 105 (PhCO), 77(Ph). NMR (25EC, CDCl3): 8.13–8.20 (m), 7.50–7.64 (m),1.36 (s, Me).

Compound 5: Hippuric acid (0.45 g, 2.5 mmol), 4-dimethylamino-1-naphthaldehyde (0.50 g, 2.5 mmol), sodium acetate (0.26 g, 3.9 mmol) and anhydrous acetic acid (10 ml, 106 mmol) were mixed and well stirred for two days. The resulting red mixture was added to cold deionized water (100 ml) and a red oil was formed. Diethylether (30 ml) was used to extract out the red product. Solvent was then removed and the red liquid was run through a silica gel column with toluene. The deep red elusion was collected and a red liquid was obtain after the solvent was removed (0.52 g).

Compound 6: 4-nitrohippuric acid (2.25 g, 10.0 mmol), p-dimethylaminobenzaldehyde (1.53 ml, 10.2 mmol), sodium acetate (0.75 g, 11.4 mmol) and anhydrous acetic acid (40 ml, 424 mmol) were mixed and well stirred for two days. The resulting deep red mixture was added to cold deionized water (150 ml) and the black solid was collected by filtration and purified by crystallization from acetone and sublimation (190 C). M.S.: 337 (P), 159 (P—NO2PhCOCO). NMR (25EC, CDCl3): 8.29 (q, 8.5 Hz), 8.12 (d, 8.0 Hz), 7.26(d, 11 Hz), 6.74 (d, 8.5 Hz), 3.12 (s, Me).

Compound 7: N-Acetylglycine (2.02 g, 17.3 mmol), p-dimethylaminobenzaldehyde (2.49 g, 16.7 mmol), sodium acetate (0.91 g,13.8 mmol) and anhydrous acetic acid (10 ml, 106 mmol) were mixed and well stirred for two days. The resulting deep red mixture was added to cold deionized water (150 ml) and the reddish solid was collected by filtration and purified by crystallization from acetone.

OLEDs were prepared using the following procedures: The ITO/Borosilicate substrates (100 Ω/square) were cleaned by sonicating with detergent for five minutes followed by rinsing with deionized water. They were then treated twice in boiling 1,1,1-trichloroethane for two minutes. The substrates were then sonicated twice with acetone for two minutes and twice with methanol for two minutes.

The background pressure prior to deposition was normally $7 \times 10^{-7}$ torr or lower and the pressure during the deposition was around $5 \times 10^{-7}$ to $1.1 \times 10^{-6}$ torr.

All the chemicals were resistively heated in various tantalum boats. TPD was first deposited at a rate from one to four Å/s. The thickness was typically controlled at 300 Å.

The electron transporting layer $Alq_3$ was doped with Compound 3. Typically, the dopant was first vaporized with the substrates covered. After the rate of the dopant was stabilized, the host material was vaporized to the certain rate. The cover over the substrates was then opened and the host and guest were deposited at the desired concentration. The rate of dopant was normally 0.1–0.2 Å/s. The total thickness of this layer was controlled at 450 Å.

The substrates were then released to air and masks were put directly on the substrates. The masks were made of stainless steel sheet and contain holes with diameters of 0.25, 0.5, 0.75, and 1.0 mm. The substrates were then put back into vacuum for further coating.

Magnesium and silver were co-deposited at a rate normally of 2.6 Å/s. The ratio of Mg:Ag varied from 7:1 to 12:1. The thickness of this layer was typically 500 Å. Finally, 1000 Å Ag was deposited at the rate between one to four Å/s.

The devices were characterized within five hours of fabrication. Typically electroluminescent spectra, I-V curves, and quantum yields were measured from direct front.

The spectra of the doped device containing Compound 3 as the dopant and of an undoped $Alq_3$ device are shown in FIG. 1. The emission from this device comes from the Compound 3 dopant.

Figure 2:
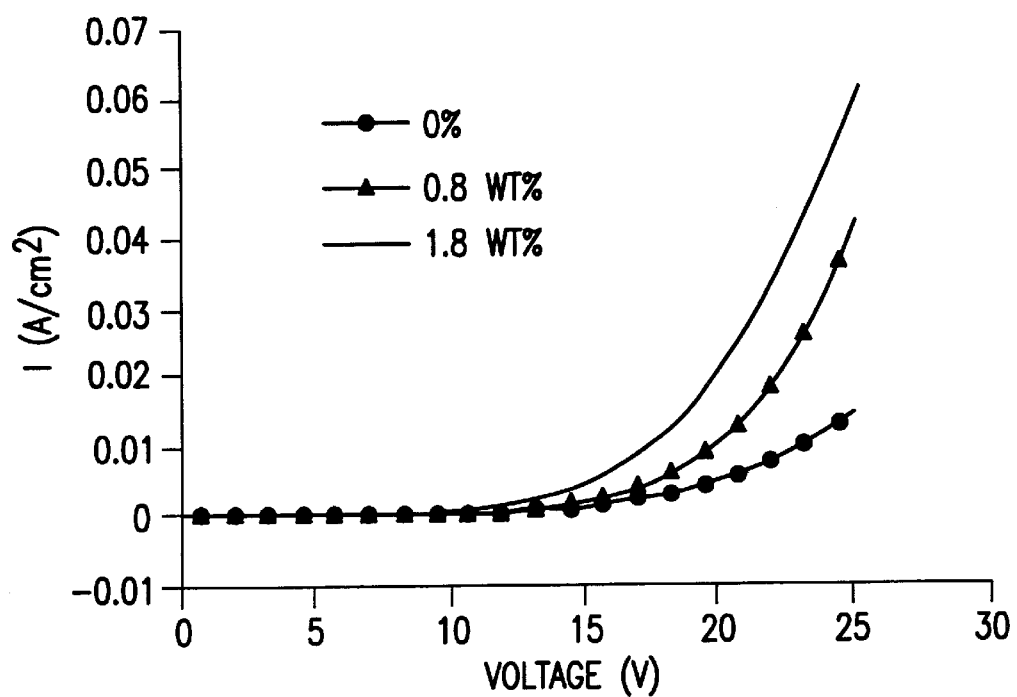
FIG. 2 shows the I-V characteristic of doped and undoped devices.

The I-V characteristics of the device shown in FIG. 2 show not only that the compound can be used in an OLED but also that such compounds are capable of provided enhanced current levels for a given voltage.

What is claimed is:

1. An organic light emitting device comprising a heterostructure for producing electroluminescence wherein the heterostructure is comprised of an emissive layer containing a dopant compound having a chemical structure of formula I:

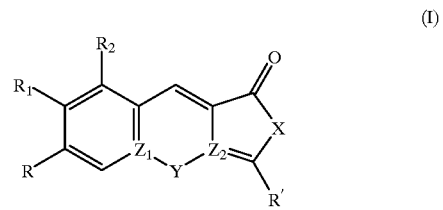

(I)

where R is hydrogen or a group which is a donor or acceptor group relative to hydrogen;

R'=alkyl or substituted or unsubstituted aryl;

$R_1$ and $R_2$ are hydrogen or are joined to form a fused aryl ring;

X is O; $NR_5$, where $R_5$ is hydrogen or substituted or unsubstituted alkyl; alkyl or substituted or unsubstituted aryl;

$Z_1$ and $Z_2$ are, independently of one another, a carbon or nitrogen atom; and Y is M, a metal atom, whenever $Z_1$ and $Z_2$ are both nitrogen atoms;

Y is O; $NR_6$, where $R_6$ is hydrogen or substituted or unsubstituted alkyl; or S; whenever either $Z_1$ or $Z_2$ is a carbon atom; or Y is absent.

2. The organic light emitting device of claim 1 wherein $Z_1$ is a carbon atom, $Z_2$ is a nitrogen atom, X is an oxygen atom and Y is absent, wherein the dopant compound has a chemical structure of formula II:

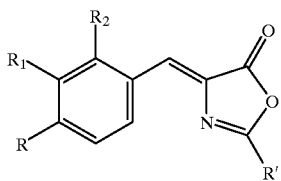

(II)

3. The organic light emitting device of claim 2 wherein the dopant compound has a chemical structure of formula II where $R_1$ and $R_2$ are hydrogen, R=H and R'=$C_6H_5$.

4. The organic light emitting device of claim 2 wherein the dopant compound has a chemical structure of formula II where $R_1$ and $R_2$ are hydrogen, R=OOCCH$_3$ and R'=$C_6H_5$.

5. The organic light emitting device of claim 2 wherein the dopant compound has a chemical structure of formula II where $R_1$ and $R_2$ are hydrogen, R=N(CH$_3$)$_2$ and R'=$C_6H_5$.

6. The organic light emitting device of claim 2 wherein the dopant compound has a chemical structure of formula II where $R_1$ and $R_2$ are hydrogen, R=C(CH$_3$)$_3$ and R'=$C_6H_5$.

7. The organic light emitting device of claim 1 wherein the dopant compound has a chemical structure of formula IV:

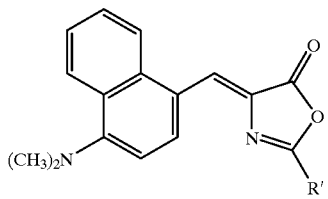

(IV)

where R'=$C_6H_5$.

8. The organic light emitting device of claim 1 wherein the dopant compound has a chemical structure of formula V:

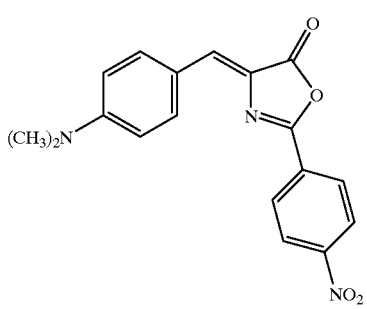

(V)

9. The organic light emitting device of claim 1 wherein the dopant compound has a chemical structure of formula VI:

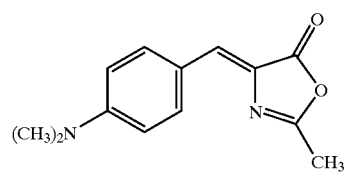

(VI)

10. The organic light emitting device of claim 1 wherein the heterostructure for producing electroluminescence is comprised of, in sequence, a substrate, a cathode layer, an electron transporting layer, a hole transporting layer and an anode layer.

11. The organic light emitting device of claim 1 wherein the heterostructure for producing electroluminescence is comprised of, in sequence, a substrate, an anode layer, a hole transporting layer, an electron transporting layer, and a cathode layer.

12. A display incorporating the organic light emitting device of claim 1.

13. A vehicle incorporating the organic light emitting device of claim 1.

14. A computer incorporating the organic light emitting device of claim 1.

15. A television incorporating the organic light emitting device of claim 1.

16. A printer incorporating the organic light emitting device of claim 1.

17. A wall, theater or stadium screen incorporating the organic light emitting device of claim 1.

18. A billboard or a sign incorporating the organic light emitting device of claim 1.

19. A method of fabricating an organic light emitting device comprising:

preparing a heterostructure for producing electroluminescence, wherein the preparation process includes the step of forming an emissive layer containing a dopant of formula I:

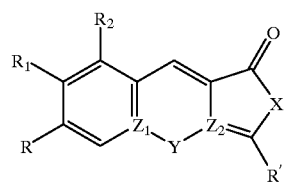

where R is hydrogen or a group which is a donor or acceptor group relative to hydrogen;

R'=alkyl or substituted or unsubstituted aryl;

$R_1$ and $R_2$ are hydrogen or are joined to form a fused aryl ring;

X is O; NR$_5$, where R$_5$ is hydrogen or substituted or unsubstituted alkyl; alkyl or substituted or unsubstituted aryl;

$Z_1$ and $Z_2$ are, independently of one another, a carbon or nitrogen atom; and Y is M, a metal atom, whenever $Z_1$ and $Z_2$ are both nitrogen atoms;

Y is O; NR$_6$, R$_6$ is hydrogen or substituted or unsubstituted alkyl; or S; whenever either $Z_1$ or $Z_2$ is a carbon atom; or Y is absent.

* * * * *

UNITED STATES PATENT AND TRADEMARK OFFICE
CERTIFICATE OF CORRECTION

PATENT No.: 6,030,715

DATED : February 29, 2000

INVENTOR(S): THOMPSON et al.

It is certified that error appears in the above-identified patent and that said Letters Patent is hereby corrected as shown below:

Column 1, line 3, please insert the following paragraph after the title:

-- GOVERNMENT RIGHTS

This invention was made with Government support under Contract No. F33615-94-1-1414 awarded by DARPA. The government has certain rights in this invention.--.

Signed and Sealed this

Tenth Day of April, 2001

Attest:

NICHOLAS P. GODICI

*Attesting Officer*    *Acting Director of the United States Patent and Trademark Office*